United States Patent [19]

Watson et al.

[11] 4,387,260

[45] Jun. 7, 1983

[54] ALKYLATION OF AROMATIC COMPOUNDS WITH SILICALITE CATALYSTS IN THE PRESENCE OF STEAM

[75] Inventors: James M. Watson; James R. Butler; Cleve H. Forward, all of Big Springs, Tex.

[73] Assignee: Cosden Technology, Inc., Dallas, Tex.

[21] Appl. No.: 327,860

[22] Filed: Dec. 7, 1981

Related U.S. Application Data

[63] Continuation-in-part of Ser. No. 255,882, Apr. 20, 1981, abandoned.

[51] Int. Cl.³ .............................................. C07C 3/52
[52] U.S. Cl. .................................. 585/467; 585/323; 252/449; 252/455 Z
[58] Field of Search ................. 585/467; 252/449, 454

[56] References Cited

U.S. PATENT DOCUMENTS

| | | | |
|---|---|---|---|
| 4,016,218 | 4/1977 | Haag et al. ........................ | 585/467 |
| 4,016,218 | 4/1977 | Haag et al. ........................ | 585/467 |
| 4,283,306 | 8/1981 | Herkes .............................. | 585/467 |
| 4,283,306 | 8/1981 | Herkes .............................. | 585/467 |

OTHER PUBLICATIONS

Flanigan et al., Nature 271, 512 (1978).
Olsen et al., J. Catalysis, 61, 390 (1980).
Bibby et al., Nature, 280, 664 (1979).
"Silicalite, A New Hydrophobic Crystalline Silica Molecular Sieve" Flanigan et al., Nature 271, 512 (1978).
"Chemical and Physical Properties of ZSM-5 Substitutional Series", Olsen et al., Jo. of Catalipir, 61, 390 (1980).
"Siliclite-2, A Silica Analogne of the Alumino-Silicate Zeolite ZSM-11", Bibby et al., Nature, 280, 664 (1979).

*Primary Examiner*—Delbert E. Gantz
*Assistant Examiner*—A. Pal
*Attorney, Agent, or Firm*—Richards, Harris & Medlock

[57] ABSTRACT

A process and apparatus for alkylating aromatic compounds with silicalite alkylation catalysts in the presence of an effective amount of water which extends the cycle length of the reaction by decreasing the rate of activity loss of the catalyst and decreases the production of unwanted by-products.

21 Claims, 1 Drawing Figure

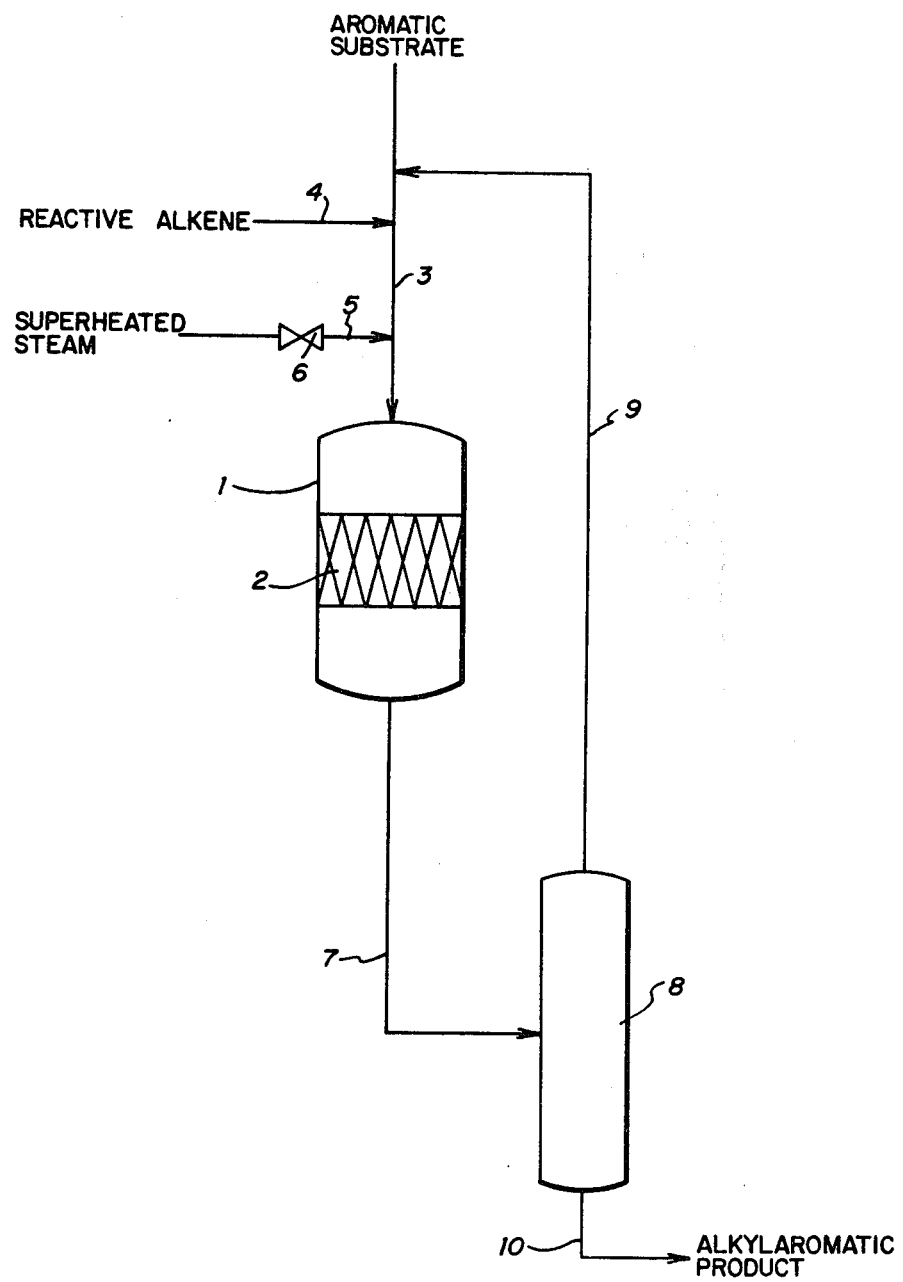

ALKYLATION OF AROMATIC COMPOUNDS WITH SILICALITE CATALYSTS IN THE PRESENCE OF STEAM

RELATED APPLICATIONS

This application is a continuation-in-part of our prior application Ser. No. 06/255,882 filed Apr. 20, 1981, now abandoned.

TECHNICAL FIELD

In one aspect, this invention relates to alkylation of aromatic compounds employing silicalite catalysts. In another aspect, this invention relates to a process whereby improved stability of silicalite catalysts and reduced production of unwanted by-products are obtained through use of steam co-feed under reaction conditions. In a further aspect, this invention relates to especially efficient processes for production of alkyl aromatics such as ethyltoluene and ethylbenzene, for example.

BACKGROUND OF THE INVENTION

Alkylaromatic compounds, such as ethylbenzene, ethyltoluene, isopropylbenzene, and the like are very important as precursors from which vinylaromatic monomers are made. The resulting vinylaromatic monomers are used to make a variety of useful polymer materials, e.g., styrenic resins. In a typical commercial process, alkylaromatic compounds are produced by catalytic alkylation at elevated temperatures. Heretofore, two major difficulties have been encountered in catalytic alkylation vapor phase processes.

The first major difficulty is the production of unwanted by-products. For example, in the production of ethyl-benzene, significant amounts of xylene isomers are also produced. Even small amounts of xylene are undesirable because separation of the xylene isomers from the ethylbenzene is exceedingly difficult due to the fact that the boiling points of the ethylbenzene and xylene isomers are substantially the same. Another problem is the attachment of more alkyl groups to an aromatic nucleus than is desired. For example, in the production of ethyltoluene a significant amount of trimethylbenzene is also produced. Again, separation of the desired product from the unwanted by-product is extremely difficult. This phenomenon, hereinafter referred to as polyalkylation, further reduces the yield of desired product. It is therefore needful, insofar as possible to prevent the formation of xylene isomers or other undesirable by-product materials during the alkylation reaction.

The second major difficulty encountered in conventional catalytic alkylation processes is rapid loss of catalytic activity. As the catalytic reaction proceeds, the activity of the catalyst in terms of the percent of the feed which is actually converted to the desired alkylaromatic product compounds progressively decreases so that after a period of time, it becomes necessary to shut down the alkylation and either replace or regenerate the catalyst. The consequent reduction in the productivity of the equipment utilized and the expense of catalyst replacement or regeneration, substantially increase the cost of producing the desired alkylaromatic compounds. As employed herein, the term "stability" refers to the ability of the catalyst to convert feedstocks to desired products measured as a function of time during which the reactions proceed.

Recently, synthetic aluminosilicate catalysts have been recognized to be useful in alkylation processes. In particular, catalysts of the ZSM-5 series have been reported to provide advantages in alkylation procedures. Such aluminosilicate materials are subject to degeneration by coking. Further, these materials are not steam stable in the sense that they are reported to rapidly lose activity when steam or water is present during the reaction. It is generally believed that the activity of these catalyst is directly proportional to the aluminum concentration and that steam progressively dealuminates the framework, thereby irreversibly deactivating the catalyst. It has also been theorized that the water combines with the aluminum present in such compositions and adversely affects the catalytically active sites of such catalysts.

There is a continuing need for an improved alkylation process and apparatus which can overcome these problems associated with the prior art.

OBJECTS OF THE INVENTION

Accordingly, it is an object of the present invention to provide an improved process and apparatus for alkylation of aromatic compounds.

Another object of the present invention is to provide an improved process and apparatus for production of alkylaromatic compounds in which the formation of by-products, such as xylene, trimethylbenzene and heavy molecules, is reduced.

It is also an object of the present invention to provide an improved process and apparatus for production of alkylaromatic compounds in which the alkylation catalyst loses its alkylation activity more slowly.

A further object of the present invention is to provide a process and apparatus for producing alkylaromatic compounds in which a higher percentage of the feed is converted to the desired alkylaromatic product.

An additional object of the present invention is to provide a process and apparatus for producing alkylaromatic compounds having an extended cycle length.

Yet another object of the present invention is to provide a process and apparatus which reduces the cost of producing the desired alkylaromatic compounds.

A still further object of the present invention is to provide an improved process for producing alkylaromatic compounds which increases the productivity of the equipment utilized.

Another object of the present invention is to provide a process and apparatus for alkylation of aromatic compounds which is particularly applicable to the production of ethylbenzene or ethyltoluene.

SUMMARY OF THE INVENTION

These and other objects are achieved by providing a process for producing alkylaromatic compounds comprising passing a reactive alkene, an aromatic substrate compound, and an effective amount of steam through a bed of silicalite alkylation catalyst under alkylation conditions and recovering the resulting alkylaromatic compound.

The objects of the invention are further achieved by providing apparatus for producing alkylaromatic compounds comprising reaction zone means, a bed of silicalite alkylation catalyst in said reaction zone means, means for introducing an alkene feed into said reaction zone means in contact with said catalyst bed, means for introducing an aromatic feed into said reaction zone means in contact with said catalyst bed, means for introducing a controlled amount of water into said reaction zone means along with said alkene feed and said aromatic feed, and means for withdrawing alkylaromatic product compounds from said reaction zone means.

The successful achievement of the objects of the invention using a combination of a silicalite alkylation catalyst and an effective amount of water (which is in the form of steam under reaction conditions) is truly unexpected and surprising because most alkylation catalysts of the prior art are acutely moisture sensitive, and the presence of ppm amounts of moisture in the catalytic alkylation zone has been found to substantially destroy the catalytic activity and prevent any useful reaction from taking place.

BRIEF DESCRIPTION OF DRAWINGS

The invention will be described in further detail with reference to the accompanying Drawing which is a schematic representation of an installation for producing alkylaromatic compounds according to the present invention.

DETAILED DESCRIPTION OF PREFERRED EMBODIMENTS

The process of the invention is applicable to a variety of aromatic feedstocks. Suitable feedstocks include benzene, toluene, ethylbenzene, naphthalene and similar compounds. Various reactive alkenes may also be used. Preferred alkene feedstocks include ethylene and propylene.

A silicalite alkylation catalyst is used in the invention. The silicalites are crystalline silica materials having a network of pores of molecular dimensions which serve as catalytically active sites. Such catalysts are known in the art; see for example U.S. Pat. No. 4,061,724, the entire disclosure of which is incorporated herein by reference. These materials are silica polymorphs as opposed to aluminosilicates. As such, their Si/Al ratios are very high since the alumina which is present merely represents impurities of the starting materials used to produce same.

Generally, the reaction is run with a substantial molar excess of aromatic substrate in order to further reduce the incidence of polyalkylation. Desirably, the mole ratio of aromatic substrate to the alkene feed will lie between about 2:1 and about 20:1, preferably between about 7:1 and about 20:1.

The water is usually introduced in the form of superheated steam. It should be recognized that some moisture will be present, in varying amounts, in the aromatic feedstock. For example, saturated benzene contains approximately 700 ppm water at ambient conditions. We have discovered that use of a steam co-feed to introduce more water than would normally be present due to that carried into the reactor with the reactants themselves can effectively increase the stability of the catalysts as reflected by percent conversion to desired products over time and decrease the amount of undesirable by-products produced. Therefore, as used herein, the term "effective amount of steam" means that amount of water, or moisture, passed into the reactor with the aromatic and alkene feed materials which will cause the particular silicalite catalyst which is employed to demonstrate improved stability and/or decreased by-product production under reaction conditions as compared to the performance of the same catalyst under the same reaction conditions in the absence of steam co-feed. Preferably, between about 20,000 ppm and about 100,000 ppm steam will be introduced into the reaction zone; most preferably between about 20,000 ppm and about 60,000 ppm.

The alkylation reaction is conducted at elevated temperature. A minimum temperature of at least about 300° C. should be used in order to maintain appreciable reaction rates. Temperatures in excess of about 600° C. desirably are avoided in order to prevent undesired side reactions which occur more readily at higher temperatures. Preferably, the inlet temperature of the alkylation reaction zone will be maintained between about 350° C. and about 500° C., most preferably between about 400° C. and about 460° C. If desired, operating temperatures may be increased as the catalyst gradually becomes deactivated.

Operating pressures within the alkylation reaction zone may vary over a substantial range. Generally, the pressure will be between about atmospheric pressure and about 25 atmospheres. Preferably, the pressure is maintained between about 10 and about 15 atmospheres.

Referring now to the drawing, reference numeral 1 designates a reactor vessel 1 defining an alkylation reaction zone. Inside reactor 1 is a bed of a silicalite alkylation catalyst 2. Only a single catalyst bed is illustrated in the schematic drawing, but it is understood that a multi-bed system comprising any desired number of catalyst beds might be used. An aromatic feed is introduced into the alkylation reactor through an inlet line 3. An alkene feed is added to the stream of aromatic compound via line 4 which flows into line 3. Similarly, a controlled proportion of superheated steam is introduced into the admixed aromatic compound and alkene feed through line 5 which leads into line 3; Valve means 6 are provided on line 5 to assure positive control of the proportion of steam introduced into the feed stream. The aromatic substrate compound and the alkene feed contact the catalyst in the reaction zone in the presence of steam and at a temperature sufficient to induce alkylation. The resulting alkylaromatic product compound is withdrawn from reactor 1 through line 7 and passed to a fractionation zone 8 where excess aromatic substrate is separated from the alkylaromatic product. The excess aromatic substrate is withdrawn as an overhead fraction from fractionation zone 8 through line 9 and recycled back to line 3. A crude alkylaromatic product fraction is withdrawn from fractionation zone 8 as a bottoms stream through line 10. If desired heavies such as diethyl benzene, produced as a by-product during ethylbenzene production, can be recovered and recycled to the inlet line 3 for more economic operation.

In its preferred embodiments, the process of the subject invention, which combines the use of silicalite catalyst and steam co-feed in alkylation reactions, provides an especially efficient procedure for producing ethylbenzene and ethyltoluene whereby the amount of the xylene, trimethylbenzene and other unwanted by-products which are difficult to separate from the product mix is reduced. More dramatically, however, the use of an effective amount of steam co-feed enhances the stability of the silicalite catalyst in that higher conversion rates can be obtained and retained over a longer period of time than when no steam is employed. This allows the cycle length of the catalyst to be extended which, of course, is of great commercial advantage. Further, the use of steam co-feed with silicalite catalyst has little or no irreversible deactivation effect on the catalyst. In other words, the same catalyst can be reused, after regeneration, without substantial loss of activity.

When employing the process of the subject invention to produce ethylbenzene or ethyltoluene from benzene and toluene aromatic feedstocks, the preferred silicalite catalysts are those having a crystallite size of less than about 8 microns and silica to alumina ratios of at least about 200. Steam co-feed in the range of from about 20,000 to about 60,000 ppm, based on the amount of aromatic compound, employed with these types of catalysts have been found to be especially beneficial. Most preferred is the use of about 40,000 ppm steam co-feed. While inlet temperatures from about 350° C. to about 500° C. can be employed, it is especially effective to operate within a range of from about 410° C. to about 475° C. Preferred reactant ratios (aromatic/alkene) are from about 7:1 to about 20:1 with preferred aromatic WHSV's ranging from about 100 to about 150. Operating pressures between about atmospheric pressure to about 25 atmospheres can be used with a range of from about 10 to about 13 being preferred.

The invention will be explained in further detail with reference to the following non-limiting examples.

EXAMPLE I

Benzene and ethylene are introduced into a reaction zone containing a bed of silicalite catalyst material having a particle size of between 12 and 20 mesh, and a Si/Al ratio of greater than about 300. The depth of the bed is approximately 8.25 cm. The benzene to ethylene molar feed ratio is approximately 16:1. Operating conditions include temperatures of about 410° C. at the inlet of the catalyst bed and outlet pressures of about 11 atmospheres with a benzene WHSV of about 110. For the 7th through 14th hours of operation, about 20,000 ppm steam, based on the weight of benzene feedstock, was introduced. During the 16th through 24th hours of operation, about 60,000 ppm steam was employed. In the 26th through 34th hours of operation, 40,000 ppm steam co-feed was employed. Finally, in the 36th through 43rd hours of operation less than about 100 ppm steam co-feed was used. The product stream from the alkylation reaction zone is analyzed by gas chromatography. The catalyst activity is determined both at the start and at the end of the run according to the following formula:

% Conversion =

$$\frac{\text{moles desired alkylaromatic compound}}{\text{moles of reactive alkene fed to reactor}} \times 100\%$$

The selectivity is determined according to the following formula:

$$\text{Selectivity} = \frac{\text{weight desired alkylaromatic compound}}{\text{total product weight}} \times 100\%$$

After a run time of 100 hours, the reaction was shut down. The initial catalyst activity was computed to be 99.9 percent conversion and the final catalystic activity was 89.7 percent conversion. The initial selectivity was 98 percent, and at the end of the run the selectivity had actually increased to 99 percent. The results of each of these runs, which employed a single catalyst sample, is set forth below:

| Catalyst Age | % Conversion | % Selectivity | Total Xylene ppm in Product | [H₂O] ppm |
|---|---|---|---|---|
| 7-14 | 86 | 99 | 489 ± 48 | 20,000 |
| 16-24 | 69 | 99 | 369 ± 32 | 60,000 |
| 26-34 | 73 → 68 | 99 | 375 ± 61 | 40,000 |
| 36-43 | 75 → 51 | 99 | 477 ± 75 | <100 |

These runs exemplify that steam co-feed significantly reduces the amount of xylene by-product which is produced, even where the comparison is between fresh versus aged catalyst material. It should be noted that while xylene content was relatively high during the first run, conversion during such run was also significantly higher than the last run.

EXAMPLE II

Toluene and ethylene are introduced into a reaction zone containing a bed of silicalite catalyst material having a particle size of between 12 and 20 mesh, and a Si/Al ratio of greater than about 300. The depth of the bed is approximately 8.0 cm. The toluene to ethylene molar feed ratio is approximately 16:1. Operating conditions include outlet pressures of about 11 atmospheres and a toluene WHSV of about 130. Two separate runs were made, one with a steam cofeed employed and one without a steam cofeed. The inlet temperature for each run was initially about 490° C. for the first 24 hours of the run and then lowered to about 470° C. for approximately the next 24 hours. The results of these runs are set forth below:

| Catalyst Age Age (hr.) | % Conversion | % Selectivity | Total Trimethyl benzene ppm in Product | [H₂O] ppm |
|---|---|---|---|---|
| 0-24.5 | 98 | 92 | 3559 ± 564 | 40,000 |
| 0-24 | 98 | 88 | 5239 ± 1039 | None |
| 26-49 | 98 | 94 | 2702 ± 122 | 40,000 |
| 24-48 | 98 | 94 | 2988 ± 122 | None |

These runs exemplify that steam co-feed significantly reduces the amount of trimethyl-benzene by-product which is produced.

EXAMPLE III

Toluene and ethylene in a molar ratio of 7:1 are reacted at a temperature ranging from about 450°–490° C. at the inlet of the catalyst bed, a pressure of about 11 atmospheres and a toluene WHSV of about 130. The catalyst employed has a mesh size between 12 and 20 and a bed depth of about 7.5 cm. A first run with fresh catalyst and no steam co-feed was performed. Conversion ranged from 98% initially to 39% after 100 hours of operation. A second run under the same reaction conditions but employing fresh catalyst of the same type was performed and in addition, 40,000 ppm steam cofeed (based on toluene) was introduced during the reaction. The initial coversion of this run was 96.8% and this was reduced to 57% after 258 hours of operation. This demonstrates that conversion (a measurement of activity of the catalyst) was maintained at a higher level after 2½ times the period of use of the catalyst, when an effective amount of steam was co-fed in the process.

EXAMPLE IV

In this experiment, inlet temperatures of from 450° to 480° C., pressures of about 11 atmospheres and aromatic to alkene molar feed ratios of approximately 8:1 are employed. Benzene is employed as the aromatic feed and ethylene as the alkene. Benzene WHSV is 110. Further, 40,000 ppm of water (based on benzene feed) is employed. The catalyst has a mesh of between 12 and 20 and a bed depth of approximately 8 cm. Conversion during the first 100 hours of operation remains at a high level of approximately 99%. Similarly, selectivity is approximately 99% after 100 hours of operation.

Next, the same catalyst used in the above-described run is regenerated. The regeneration procedure employed here can generally be described as follows. First, the catalyst material is heated to 480° C. in the presence of nitrogen gas. After three hours of such treatment, steam is introduced at the rate of 28 WHSV. After 30 minutes, nitrogen is cut back to 12 WHSV and steam to 5 WHSV. At the end of 10 hours, steam is raised back to a level of 28 WHSV, nitrogen to 24 WHSV and air flow is introduced at 0.5 WHSV. Thereafter, the steam and nitrogen are slowly eliminated from the system and air flow increased stepwise over a period of three hours. Total regeneration time is about 18 hours.

Using the regenerated catalyst employed in the run set forth above, a second run without steam co-feed is performed at inlet temperatures in the range of 450° C. to 500° C., pressures of about 11 atmospheres and a toluene to ethylene molar feed ratio of 16. Toluene WHSV is 130. Conversion remained at greater than or equal to 98% during 160 hours of operation using the regenerated catalyst. This demonstrates that use of steam co-feed does not significantly irreversibly affect the activity of the silicalite catalyst material. However, selectivity ranged from an initial approximate 88% to a final 92% after 161 hours of operation.

The foregoing embodiments have been set forth solely as examples of the invention and are not intended to be limiting. Since modifications of the disclosed embodiments incorporating the spirit and substance of the invention may occur to persons skilled in the art, the scope of the invention is to be construed with respect to the appended claims.

We claim:

1. A process for producing alkylaromatic compounds comprising passing an aromatic compound, a reactive alkene and an effective amount of water through a bed of a silicalite alkylation catalyst at alkylation conditions and recovering the resulting alkylaromatic compound, the presence of said water effecting enhanced catalytic conversion to the desired alkylaromatic compound.

2. A process according to claim 1, wherein said water is introduced in the form of superheated steam.

3. A process according to claim 1, wherein said aromatic compound, said reactive alkene and said water are admixed prior to introduction into a reaction zone containing the alkylation catalyst bed.

4. A process according to claim 1, wherein a molar excess of aromatic compound is introduced into the reaction zone.

5. A process according to claim 4, wherein the mole ratio of aromatic compound to reactive alkene lies in the range from about 2 to about 20.

6. A process according to claim 1, wherein said reactive alkene is ethylene.

7. A process according to claim 6, wherein said aromatic compound is benzene.

8. A process according to claim 6, wherein said aromatic compound is toluene.

9. A process according to claim 1, wherein the temperature in the reaction zone is maintained between about 300° C. and about 600° C.

10. A process according to claim 9, wherein the temperature in the reaction zone is maintained between about 400° C. and about 460° C.

11. A process according to claim 1, wherein the pressure in the reaction zone is maintained between about 3 and about 25 atmospheres.

12. A process according to claim 11, wherein the pressure in the reaction zone is maintained between about 10 and about 15 atmospheres.

13. A process according to claim 1, wherein from about 20,000 ppm to about 100,000 ppm water based on the weight of the aromatic compound are introduced into the reaction zone.

14. A process according to claim 13, wherein about 40,000 ppm water based on the weight of the aromatic compound are introduced into the reaction zone.

15. A method of reducing the loss of activity of silicalite catalyst materials employed in alkylation of aromatic substrates comprising introducing an effective amount of steam into the reaction zone during alkylation.

16. The method of claim 15, wherein the amount of steam employed is in the range of from about 20,000 to about 60,000 ppm based on the weight of said aromatic substrate.

17. The method of claim 16, wherein said steam is introduced in an amount of about 40,000 ppm, based on the weight of said aromatic substrate.

18. A method for reducing the production of undesired by-products during alkylation of aromatic substrates using silicalite catalysts comprising introducing an effective amount of steam into the reaction zone during the alkylation process.

19. The method of claim 18, wherein said undesired by-products comprise xylene or trimethylbenzene.

20. The method of claim 19, wherein the amount of steam employed is in the range of from about 20,000 to about 60,000 ppm, based on the weight of aromatic substrate.

21. The method of claim 20, wherein the amount of steam employed is 40,000 ppm, based on the weight of aromatic substrate.

* * * * *